(12) United States Patent  
Elenbaas

(10) Patent No.: US 9,030,490 B2
(45) Date of Patent: May 12, 2015

(54) GENERATING COMPOSITE MEDICAL IMAGES

(75) Inventor: Thijs Elenbaas, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 110 days.

(21) Appl. No.: 13/387,386

(22) PCT Filed: Sep. 17, 2010

(86) PCT No.: PCT/IB2010/054207
§ 371 (c)(1),
(2), (4) Date: Jan. 27, 2012

(87) PCT Pub. No.: WO2011/039672
PCT Pub. Date: Apr. 7, 2011

(65) Prior Publication Data
US 2012/0176406 A1 Jul. 12, 2012

(30) Foreign Application Priority Data
Sep. 29, 2009 (EP) ..................... 09171624

(51) Int. Cl.
| G09G 5/00 | (2006.01) |
| A61B 6/00 | (2006.01) |
| A61B 6/03 | (2006.01) |
| G06K 9/20 | (2006.01) |

(52) U.S. Cl.
CPC .............. *A61B 6/5241* (2013.01); *A61B 6/032* (2013.01); *A61B 6/4085* (2013.01); *G06K 2009/2045* (2013.01); *G06T 2200/32* (2013.01); *G06T 2207/10072* (2013.01); *G06T 2207/10116* (2013.01); *G06T 2207/30004* (2013.01)

(58) Field of Classification Search
CPC ........... G06T 15/08; G06T 19/00; G06T 5/50; G06T 207/20221; G06T 2210/41; G06T 2207/30004; G06T 2207/20016; G06T 15/04; G06T 15/30; G06T 2207/20144; G06T 2207/20212; G06T 2207/30101; G06T 2210/62; G06T 2219/008; G06T 2219/028; G06T 7/0024; G06T 7/0038; G06T 11/60; G06T 15/503; G06T 2207/10116; G06T 7/0012; G06T 7/602; G06T 2207/10088; G06T 2207/30068; G06T 2207/10081; G06T 2207/10104; G06T 2207/30096; G06T 2207/30204; G06T 7/0081; G06T 7/0085; G09G 5/14; G09G 2340/10; G09G 2340/125
USPC ............ 345/630, 629, 419; 382/284; 600/407
See application file for complete search history.

(56) References Cited

U.S. PATENT DOCUMENTS

| 7,095,905 | B1 | 8/2006 | Peterson | |
| 8,400,470 | B2 | 3/2013 | Shields et al. | |
| 8,594,458 | B2 | 11/2013 | Wiesenfarth | |
| 2002/0120195 | A1 | 8/2002 | Hossack et al. | |
| 2005/0226531 | A1* | 10/2005 | Silverstein et al. | 382/284 |
| 2007/0165141 | A1* | 7/2007 | Srinivas et al. | 348/571 |
| 2008/0030573 | A1 | 2/2008 | Ritchey | |
| 2008/0118138 | A1* | 5/2008 | Zingaretti et al. | 382/132 |
| 2008/0125639 | A1 | 5/2008 | Ding | |
| 2008/0152088 | A1 | 6/2008 | Wang | |
| 2009/0012383 | A1* | 1/2009 | Virtue et al. | 600/407 |
| 2009/0198123 | A1 | 8/2009 | Aoyagi et al. | |
| 2010/0172472 | A1 | 7/2010 | Ermes | |
| 2011/0188726 | A1 | 8/2011 | Nathaniel et al. | |
| 2012/0105469 | A1 | 5/2012 | Pascucci | |
| 2014/0005486 | A1 | 1/2014 | Charles | |
| 2014/0240355 | A1 | 8/2014 | Isaacs et al. | |
| 2014/0267586 | A1 | 9/2014 | Aguilar et al. | |
| 2014/0300687 | A1 | 10/2014 | Gillard et al. | |

FOREIGN PATENT DOCUMENTS

| DE | 4102729 A1 | 8/1991 |
| JP | 2002094772 A | 3/2002 |
| WO | 2009055913 A1 | 5/2009 |

OTHER PUBLICATIONS

Wei, Guo-Qing et al, "A New Fully Automatic Method for CR Image Composition by White Band Detection and Consistency Rechecking", Proceedings of the International Soc. for Optical Engineering (SPIE), vol. 4322, No. 3, Jul. 1, 2001, pp. 1570-1577.

"Lift the Strip!", Internet Citation, Dec. 19, 2013, Retrieved From the Internet: URL: http://www.mada.org.il/brain/strip-e.html, XP007922461, 1 page.

* cited by examiner

*Primary Examiner* — Devona Faulk
*Assistant Examiner* — Nicole Gillespie

(57) ABSTRACT

The invention relates to generating a composite medical image combining at least first and second image data. Particularly, the invention relates to a medical imaging system for generating a composite medical view or image combining at least first and second image data as well as a method for generating a composite medical image. In order to provide a combination of image data providing improved perceptibility and enhancing the use of acquired image data, a medical imaging system for generating a composite medical view/image combining at least first and second image data, comprising an image acquisition device, a data processing unit and a display device, a medical imaging system and a method for generating a composite medical image combining at least first and second image data provided, the method comprising the following steps: a) selecting first image data of a first image (212) and second image data of a second image (214); b) registering the first and the second image data; c) determining a boundary connecting sector connecting adjacent boundaries of the first image and the second image; d) generating a separator (218) on behalf of the image data of the boundary connecting sector; e) combining image data of the first image and the second image with image data of the separator to a combined image data; and f) displaying the combined image comprising the separator (218).

21 Claims, 12 Drawing Sheets

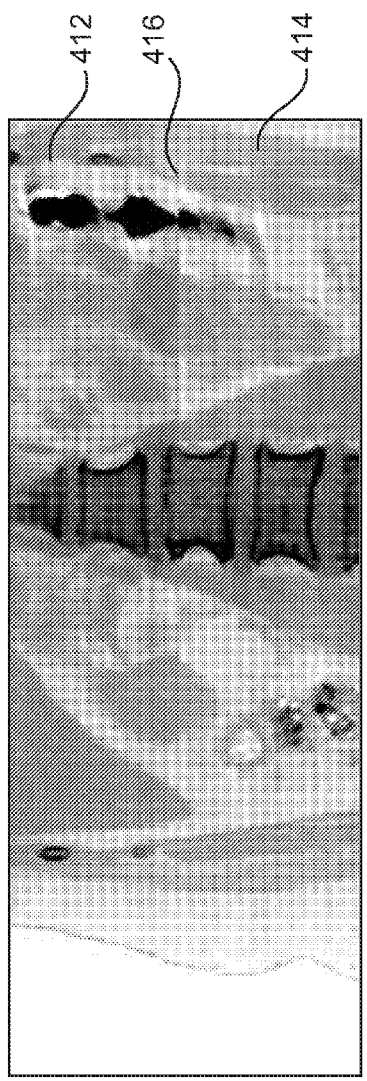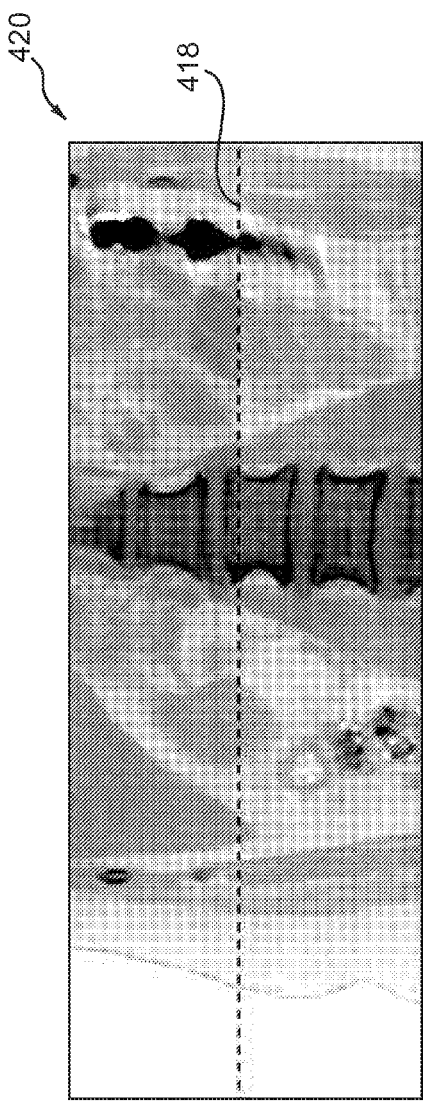

GENERATING COMPOSITE MEDICAL IMAGES

FIELD OF THE INVENTION

The invention relates to generating a composite medical view combining at least first and second image data. Particularly, the invention relates to a medical imaging system for generating a composite medical image combining at least first and second image data as well as a method for generating a composite medical view.

BACKGROUND OF THE INVENTION

In clinical applications, a single view or image may not be sufficient to view or image the complete desired body region. Thus, two or more, in other words, multiple, scans are combined to represent the full desired body region. The necessity to combine several images may for example be due to image acquisition aspects, such as the size of available image detectors. For example, the size and resolution of X-ray images is defined among other aspects primarily by the size of the detector. The step of combining several images is also referred to as stitching images together. But it has been shown that due to different reasons, for example due to artefacts or movement during the image acquisition, two adjacent images may not perfectly connect at their contacting edges. These contacting edges are also referred to as interface of the two adjacent images. The eye is very sensitive in identifying discontinuities along a straight interface and even very small jumps in intensity may be deemed unacceptable, for example by surgeons in a hospital. However, differences in intensity along the interface can induce a sense of (sometimes serious) image artifacts, more than is warranted by the actual intensity jump over the interface. Further, differences in intensity along the interface, may also add to fatigue and even loss of concentration with respect to the user, for example clinical staff. Therefore, it is known to blend two images together in an overlap region. But this requires a larger image area than the actual image area used for the combination, in other words, the step of blending images requires more individual images because of the necessary overlap. Another disadvantage is that blending images together may remove or distort clinically relevant data.

SUMMARY OF THE INVENTION

Hence, there may be a need to provide a combination of image data providing improved perceptibility and enhancing the use of acquired image data.

According to an exemplary embodiment of the invention, a method for generating a composite medical view combining at least first and second image data is provided that comprises the following steps: a) selecting first image data of a first image and second image data of a second image; b) registering the first and second image data; c) determining a boundary connecting sector connecting adjacent boundaries of the first image and the second image; d) generating a separator on behalf of the image data of the boundary connecting sector; e) combining image data of the first image and the second image with image data of the separator to a combined image data; and f) displaying the combined image comprising the separator.

The separator provides the effect that the two image regions are visually decoupled because the separator represents the boundary connecting sector connecting adjacent boundaries of the first image and the second image. Thus, the separator provides the possibility to effectively remove the visibility of small discontinuities normal to the separator. Differences in the intensity of the two adjacent image regions are not visible any more. Further, patient data contained in the acquired image data is not being removed as is the case, for example, when blending images together in an overlap region. As a further advantage, the user, for example a physician is provided with information where two or more volume segments are connected. This information is provided by displaying the separator in the combined image.

It is noted that according to another exemplary embodiment, the term view relates to, for example, an image, such as an image displayed on a monitor.

According to another exemplary embodiment, the term view refers to a projection of a 3D volume.

Hence, the terms first and second image data refers to both data for 2D images and dada for 3D volumes.

In another exemplary embodiment, the image data is two-dimensional image data. For example, the separator can be a straight or curved or otherwise shaped line.

In a further exemplary embodiment, the image data is three-dimensional image data. For example, the separator can be a straight plane or a curved or otherwise shaped spatial layer.

In a further exemplary embodiment, the separator can present the interface of two adjacent volumes.

In a further exemplary embodiment, the separator can present the area or space between the two adjacent volumes, for example, in case the first and second image data are registered such that a gap exists between the two images. For example, the gap can have the shape of a wedge, thus leading to a boundary connecting sector having the form of a wedge, too. It is then possible, for example, to generate a separator following the wedge-like form of a boundary connecting sector.

In another exemplary embodiment, the separator can be adapted such that a misleading or disturbing form of the boundary connecting sector is at least partially equalled.

According to another exemplary embodiment, the combined image can be a combination of more than two images, for example, three or four images. The image can be combined, for example, out of images arranged one next to another, for example, in a row. The images can also be arranged in a certain pattern, such as around a center point.

According to another exemplary embodiment, a method is provided wherein the step c) of determining the boundary connecting sector comprises the following sub-steps. First, a common image region of the first image data overlapping with the second image data is determined and the common image region of the second image data overlapping with the first image data is determined. Next, cutting data in the common image regions is determined. Then, the first image data is adapted by cutting the first image data according to the cutting data removing the overlapping region of the first image data and the second image data is adapted by cutting the second image data according to the cutting data removing the overlapping region of the second image data. Further, the cutting data is determined as boundary connecting sector. Still further, the separator is generated adapted to the cutting data.

By determining the overlap of images to be combined, it is also possible to use images which have been acquired according to conventional acquisition procedures where it is common to provide an overlap of the images. As an advantage, the step of blending commonly used in such cases is not necessary any more.

According to an exemplary embodiment, the cutting data can be a cutting plane in case the image data is three-dimensional image data or a cutting line in case of two-dimensional image data.

According to another exemplary embodiment, the step e) of combining image data of the first image and the second image with image data of the separator to the combined image data comprises a step of displacing the adapted first image data and the adapted second image data in relation to each other and the step of locating the separator such that the separator is located at least outside the adapted first image.

According to a further exemplary embodiment, the separator can also be located outside the adapted second image, in other words, between the first and the second image.

This provides the possibility to show both the image parts to be combined and the separator without hiding any clinically relevant data contained in the acquired image data.

According to another exemplary embodiment, the image data is two-dimensional image data.

For example, the 2D image data can be a projection of three-dimensional volume information.

For example, the image data can be acquisition by X-ray, such as a BrightView XCT scan.

According to another exemplary embodiment, the separator is a line.

A line provides a separator minimizing the risk of misleading interpretation by the user.

For example, the separator can be adapted to the adjacent image data. For example, the line can be adapted concerning brightness or colour. For example, in an image with a dark back ground showing image information in rather bright colors, the separator can be shown in bright colors or in a brighter grey scale value in case of a grey scale image.

According to another exemplary embodiment, the separator is a striped line.

According to another exemplary embodiment, the line can be a dotted line.

Dotted or striped lines give the greatest sense of observing an uninterrupted volume to the user, while still visually hiding discontinuities of the combined image halves.

According to another exemplary embodiment, the separator is a coloured line. Also, a coloured and striped line may be used. Further, for example, the line can be adapted to the location on the screen or the image to fulfill its function of hiding or reducing discontinuities along the interface due to the particular sensitivity of the user's eye. For example, the line can be differently adapted along its extension.

According to an exemplary embodiment the separator can be adapted along its extension in relation to the adjacent image content, for example depending on image parameters such as brightness, contrast or colours etc.

According to an exemplary embodiment of the invention, a medical imaging system for generating a composite medical view or image, combining at least first and second image data is provided comprising an image acquisition device, a data processing unit and a display device. The image acquisition device is arranged to acquire at least a first and second image. The data processing unit is adapted to receive first image data of a first selected image and second image data of a selected second image from the image acquisition device. The data processing unit is further adapted to register the first and the second image data. The data processing unit is adapted to determine a boundary connecting sector, connecting adjacent boundaries of the first image and the second image and to generate a separator on behalf of the image data of the boundary connecting sector. The data processing unit is further adapted to combine image data of the first image and the second image with image data of the separator to a combined image data. The display device is arranged to display the combined image comprising the separator.

According to another exemplary embodiment, an interface unit is provided, which interface unit is adapted for the selection of the first image and the second image by the user.

According to an exemplary embodiment, the data processing unit is adapted to determine a common image region of the first image data overlapping with the second image data and to determine a common image region of the second image data overlapping with the first image data. The data processing unit is also adapted to determine cutting data in a common image region and to adapt the first image data by cutting the first image data according to the cutting data removing the overlapping region of the first image data and to adapt the second image data by cutting the second image data according to the cutting data removing the overlapping region of the second image data. The data processing unit is further adapted to determine the cutting data as boundary connecting sector and to generate the separator adapted to the cutting data.

According to an exemplary embodiment, the image acquisition device is an X-ray acquisition device.

For example the X-ray acquisition device is an XCT scan. The image data can be two-dimensional image data. For example, the 2D image data can be a projection of three-dimensional volume information acquired by an X-ray image acquisition process.

In another exemplary embodiment of the present invention, a computer program or a computer program element is provided that is characterized by being adapted to execute the method steps of the method according to one of the preceding embodiments, on an appropriate system according to one of the preceding embodiments.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be down loaded into the working memory of a data processor from such a network. According to a further exemplary embodiment of the present invention, a medium for making a computer program element available for down loading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

BRIEF DESCRIPTION OF THE DRAWINGS

The aspect defined above and further aspects, features and advantages of the present invention can also be derived from the examples of embodiments to be described herein after and are explained with reference to examples of embodiments, but to which the invention is not limited. The invention will be described in more detail hereinafter with reference to the drawings.

FIG. 9 shows another example for two adjacent images with discontinuities in intensity along a horizontal interface;

FIG. 10 shows a combined image, according to the invention, comprising a separator, based upon the images shown in FIG. 9;

DETAILED DESCRIPTION OF EMBODIMENTS

Figure 1:
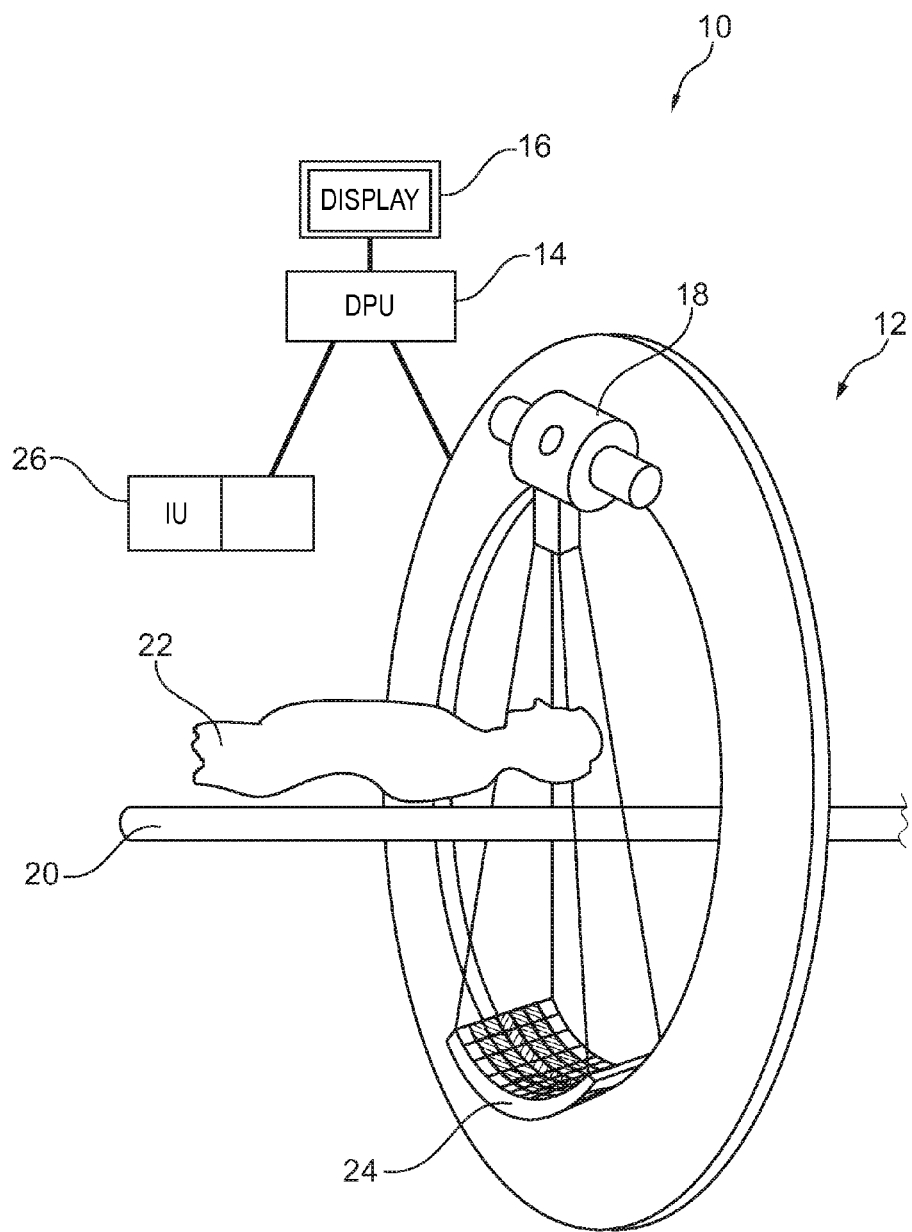
FIG. 1 schematically shows a medical imaging system.

FIG. 1 schematically shows a medical imaging system 10 for generating a composite medical view/image, combining at least first and second image data. The medical imaging system 10 comprises an image acquisition device 12, a data processing unit 14 and a display device 16.

It is noted that the term view relates to, for example, an image, such as an image displayed on a monitor. Further, the term view also refers to a projection of a 3D volume. Still further, the terms first and second image data refers to both data for 2D images and dada for 3D volumes.

For example, the medical imaging system is an X-ray imaging system, comprising a source of X-ray radiation 18 provided to generate X-ray radiation. A table 20 is provided to receive a subject to be examined, for example a patient 22. Further, an X-ray image detection module 24 is located opposite the source of X-ray radiation 18, i.e. during the radiation procedure, a subject is located between the source of X-ray radiation 18 and detection module 24. The latter is sending data to the data processing unit 14 which is connected to both, the detection module 24 and the radiation source 18. The data processing unit 14 is located in the vicinity of the table 20, for example integrated into a common housing. Of course, it could also be located at different places, such as a different room. Furthermore, the display 16 is arranged in the vicinity of the table 20 to display information to a person operating the X-ray imaging system, for example a clinician such as a surgeon or a cardiologist, for example. Preferably, the display device 16 is movably mounted to allow for an individual adjustment, depending on the examination situation. Also, an interface unit 26 is arranged to input information or commands by the user. Basically, the image detection module 24 generates image data by exposing the subject to X-ray radiation, wherein said images are further processed in the data processing unit 14. It is noted that the example shown is a so-called CT-type X-ray image acquisition device. Of course, the invention also relates to other types of X-ray image acquisition devices, such as C-type X-ray image acquisition devices. Of course, instead of using X-ray radiation to acquire image data, the invention also relates to other image acquisition procedures, such as photography or ultrasound imaging.

The image acquisition device 12 is arranged to acquire at least a first and a second image. The data processing unit 14 is adapted to receive first image data of a first selected image and second image data of a selected second image from the image acquisition device, to register the first and the second image data, to determine a boundary connecting sector connecting adjacent boundaries of the first image and the second image, to generate a separator on behalf of the image data of the boundary connecting sector, and to combine image data of the first image and the second image with image data of the separator to combine image data. The display device 16 is arranged to display the combined image comprising a separator. The procedure, according to the invention is described in more detail below.

Figure 2:
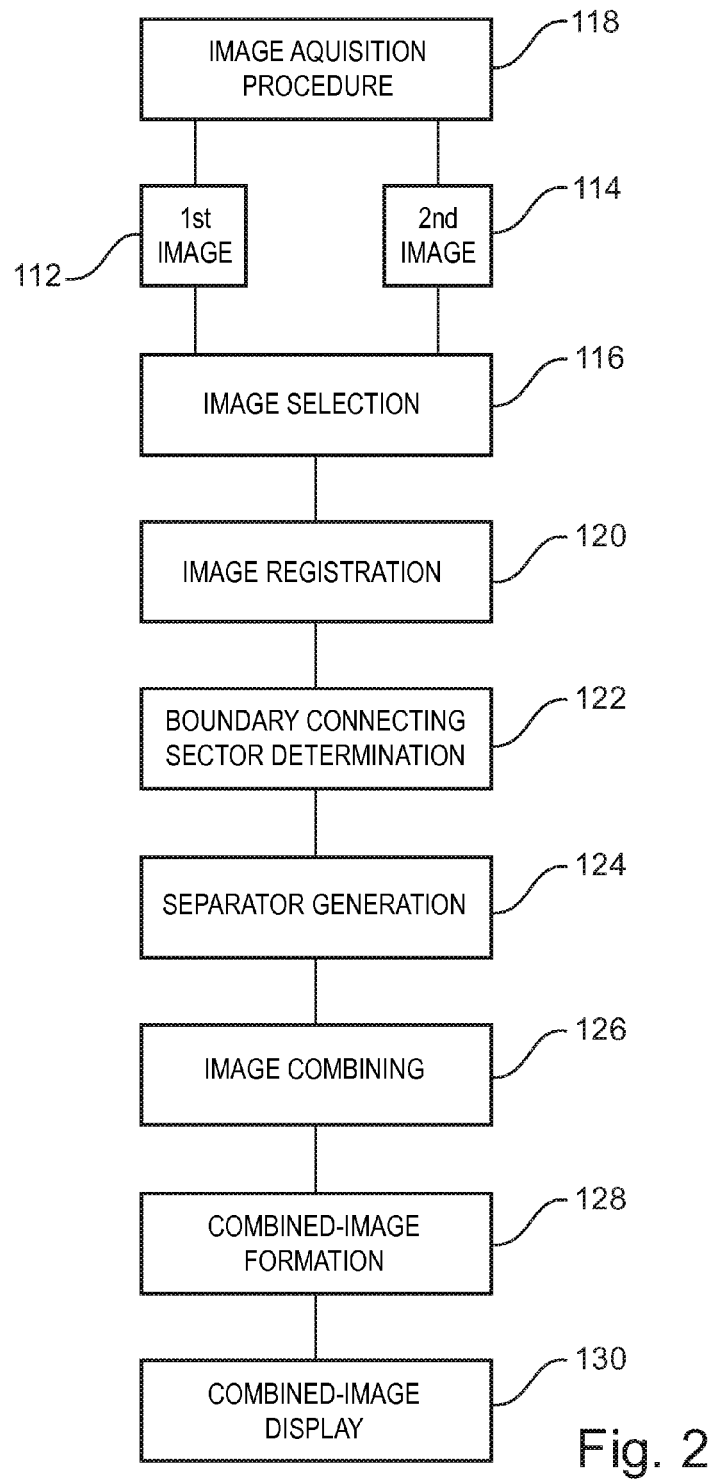
FIG. 2 schematically shows basic steps of a method for generating a composite medical view or image.

FIG. 2 schematically shows basic method steps for generating a composite medical image, combining at least first and second image data. First, image data of a first image 112 and second image data of a second image 114 are selected in a step 116. For example, these images 112, 114 may have been acquired prior to the selecting step in an image acquisition procedure 118. This image acquisition procedure can also be referred to as a prior step that is a step performed independent of the other method steps. In exemplary embodiment, the image acquisition step 118 may also be referred to as a part of the method steps.

Further, in a registration step 120, the first and the second image data are registered. Then, in a determination step 122, a boundary connecting sector connecting adjacent boundaries of the first image 112 and the second image 114 is determined. Then, in a generating step 124, a separator is generated on behalf of the image data of the boundary connecting sector. In a combining step 126, image data of the first image and the second image is combined with image data of the separator to a combined image data 128. Further, in a display step 130, the combined image comprising the separator is displayed.

For example, the image data can be two-dimensional image data such that the separator can be a straight or curved line.

In case the image data is a three-dimensional image data, the separator can be a straight or curved or otherwise shaped plane.

The separator can present the interface of two adjacent volumes.

Of course, the combined image can be a combination of more than two images, for example three or four images. The image can be combined, for example out of images arranged one next to another, for example in a row, or arranged in certain patterns, such as a round or center point.

Figure 3:
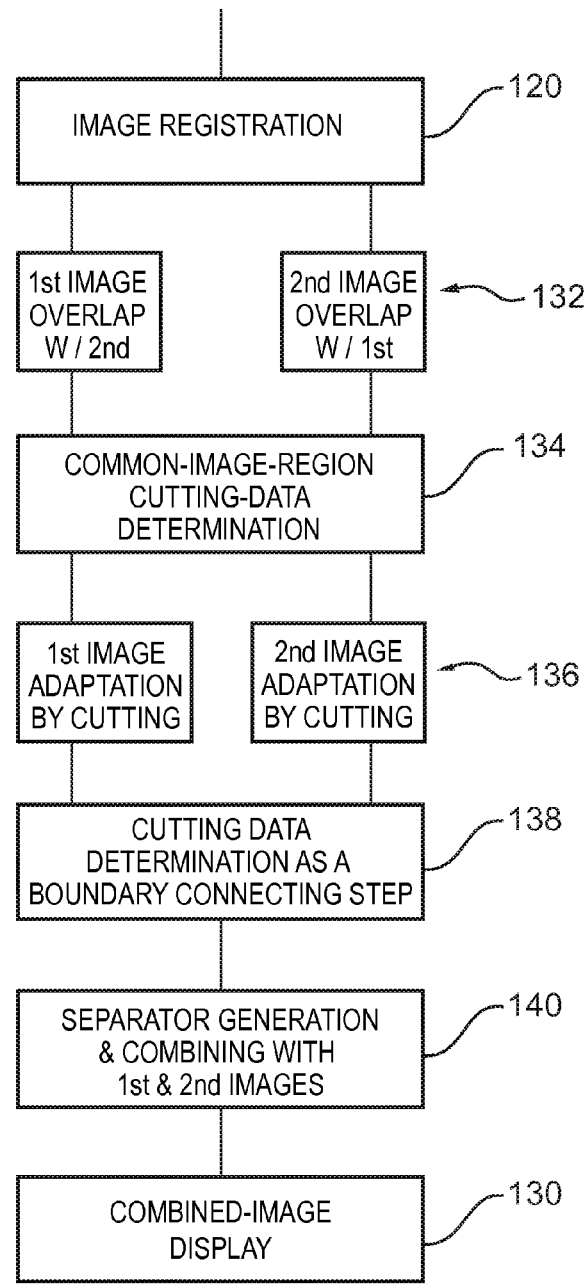
FIG. 3 schematically shows sub steps of an exemplary embodiment of the method shown in FIG. 2.

FIG. 3 shows an exemplary embodiment of the steps 122 and 124. According to this exemplary embodiment, the step 122 of determining the boundary connecting sector comprises several sub steps, as described in the following. Following to the step 120 of registering the first and the second image data, in a determining step 132, a common region of the first image data overlapping with a second image data is determined and an image region of the second image data overlapping with the first image data is also determined. Next, in a determining step 134, cutting data the common image region is determined. Then, in an adapting step 136, the first image data is adapted by cutting the first image data according to the cutting data removing the overlapping region of the first image data and the second image data is adapted by cutting the second image data according to the cutting data removing the overlapping region of the second image data. Further, in a determining step 138, the cutting data is determined as a boundary connecting step. Further, the step 124 of generating the generator comprises generating the separator adapted to the cutting data. Finally, the combined image data comprising the separator is displayed in the display in step 130.

Figure 4:
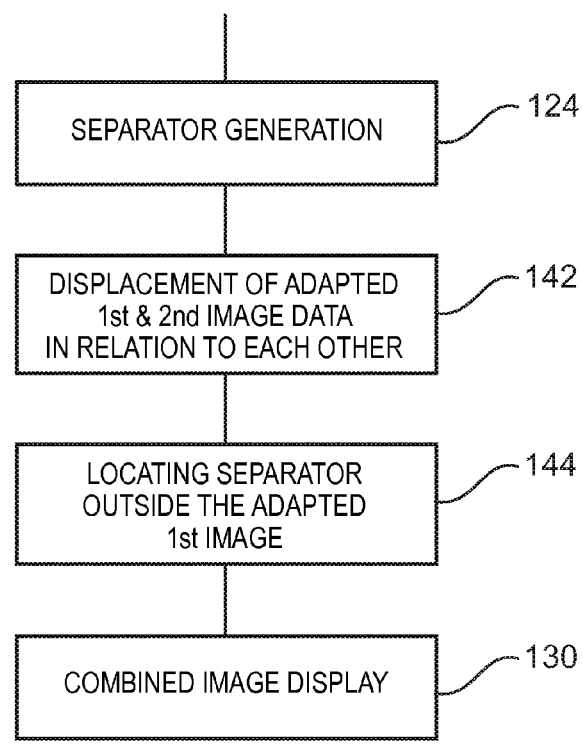
FIG. 4 shows additional sub steps of the methods shown in FIGS. 2 and 3.

FIG. 4 shows another exemplary embodiment of the method, basically described in FIG. 2. Following the generating step 124 of FIG. 2, referring to generating a separator on behalf of the image data of a boundary connecting sector, or also following the determination step 140 described in FIG. 3, referring to the generating step, comprising generating the separator adapted to the cutting data, the step 128 of combining image data of the first image and the second image with image data of the separator to the combined image data comprises a displacing step 142 where the adapted first image data and the adapted second image data are displaced in relation to each other. It also comprises a separator placement step 144 in which the separator is located such that the separator is located outside the adapted first image. Further, the displaying step 130 is provided to display the combined image comprising the separator.

According to an example, the separator can also be located outside the adapted second image, in other words, between the first and the second image.

FIGS. 5 to 10 show exemplary embodiments of two adjacent images having discontinuities along a straight interface which in the FIGS. 5 to 10 is arranged horizontally. For a better understanding, the two images are shown adjacent to each other in one example and as a combined image comprising a separator according to the invention.

Figure 5:
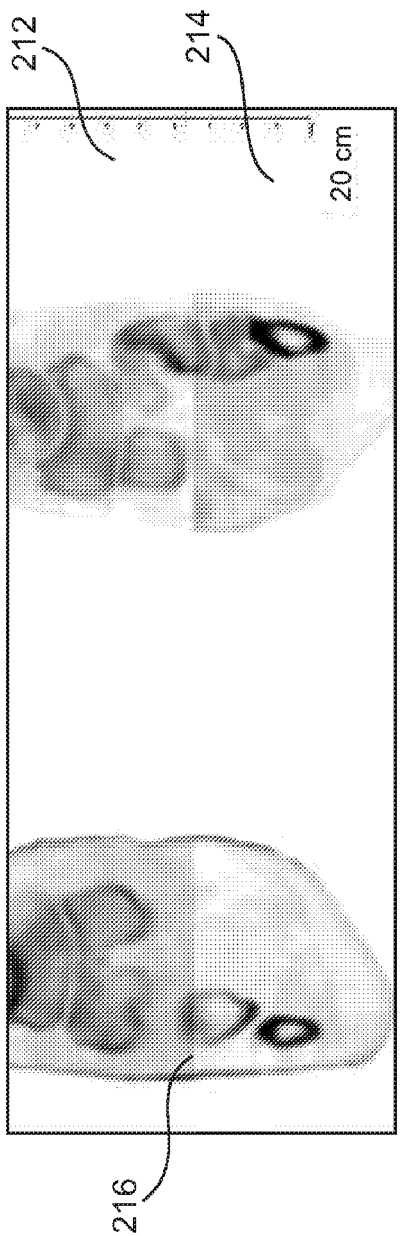
FIG. 5 shows an exemplary embodiment of 2 connecting images with discontinuities in intensity along a straight interface.
Figure 6:
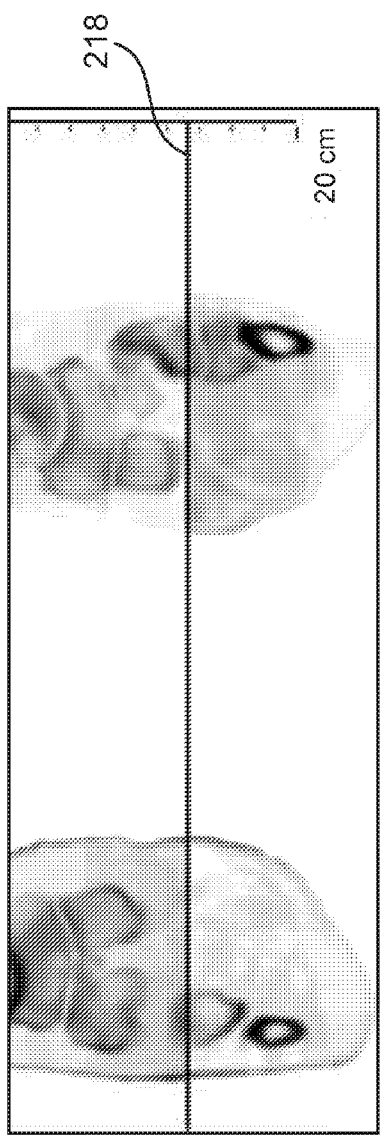
FIG. 6 shows the two adjacent images of FIG. 5 in a combined image comprising a separator.

A first example is shown in FIGS. 5 and 6, showing two images 212 and 214 arranged as horizontal stripes with a strict interface 216 showing discontinuities in intensity which may be deemed unacceptable by a user. According to the invention, a separator 218 is provided in FIG. 6, eliminating or at least significantly reducing the visible discontinuities along the straight interface 216. In the example shown in FIG. 6, the separator 218 is shown as a medium line, for example in a colour not used in the combined images 212 and 214. For example, in case the images 212 and 214 are X-ray images shown in a grey scale value, the separator 218 can be shown as a yellow line.

Figure 7:
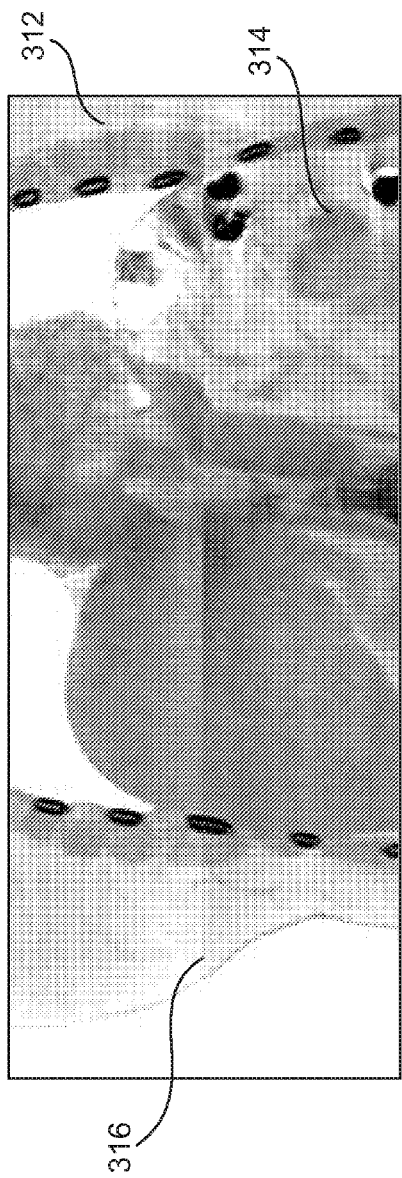
FIG. 7 schematically shows another example of two adjacent images with intensity differences along a horizontal interface.
Figure 8:
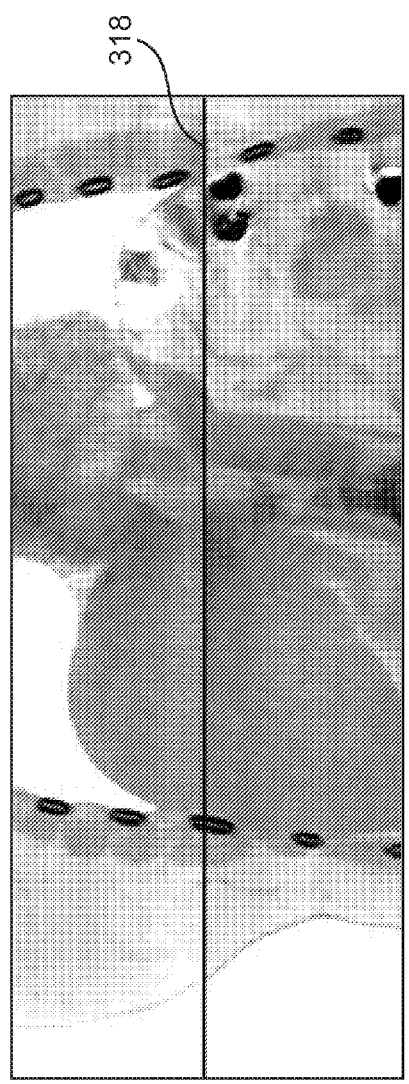
FIG. 8 schematically shows a combined image, according to the invention, based on the images shown in FIG. 7, comprising a separator.
Figure 11:
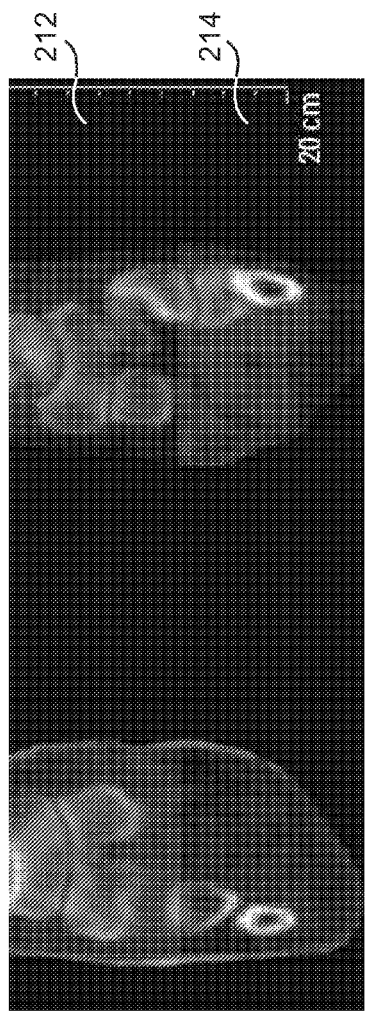
FIGS. 11 to 16 show photographic images of X-ray images according to FIGS. 5 to 10 respectively.
Figure 12:
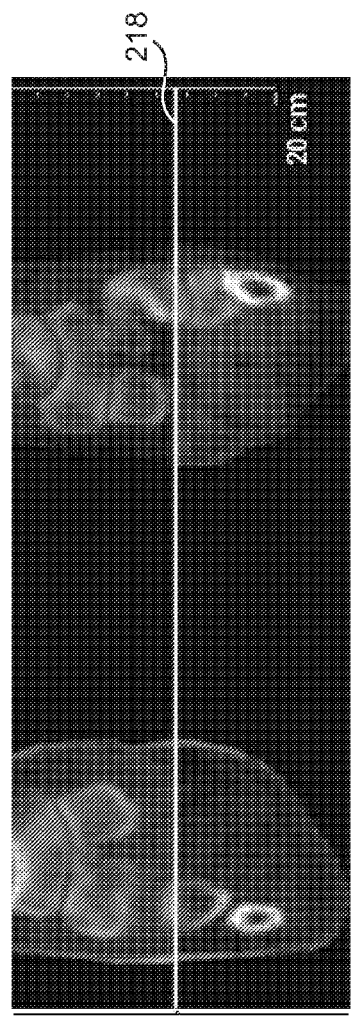
Figure 13:
Figure 14:
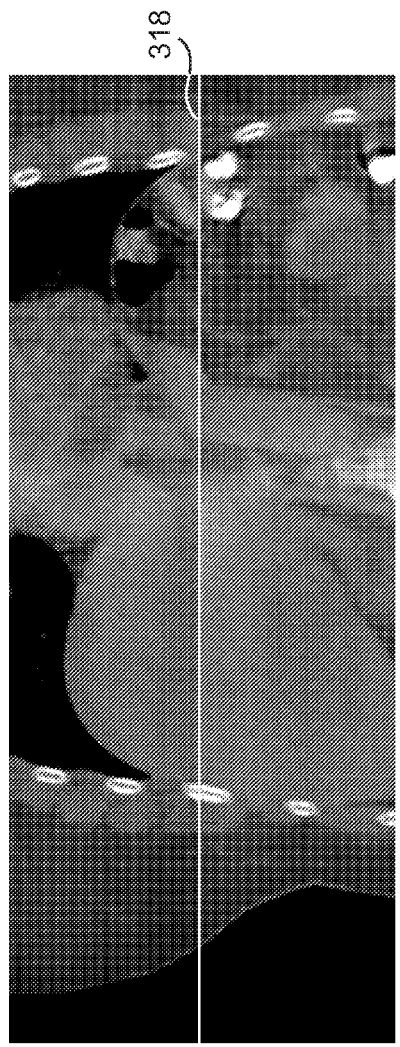
Figure 15:
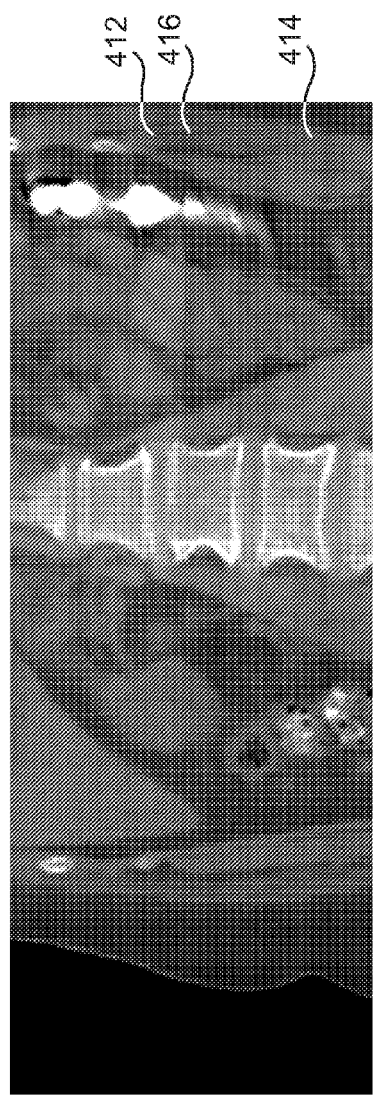
Figure 16:
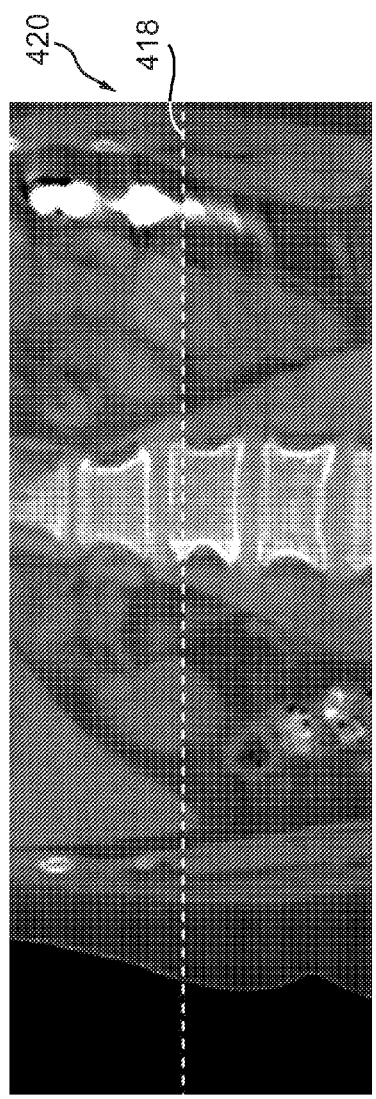

According to the example shown in FIGS. 7 and 8, FIG. 7 shows a first image 312 and a second image 314 arranged underneath connected by a straight interface 316 arranged in a horizontal direction. As can be seen, the two images 312 and 314 show differences in their intensity although the adjacent image regions refer to the same body region. According to the invention, a separator 318 is shown in FIG. 8 displaying the combined image comprising the separator 318. In this example, the separator 318 is shown as a solid white thin line.

In a further exemplary shown in FIGS. 9 and 10, a first image 412 and a second image 414 are arranged adjacent to each other, connected by an interface 416. The interface 416 can be identified in FIG. 9 due to the different image intensities along the straight interface 416. According to the invention, after selecting the first image data of a first image 412 and second image data of a second image 414 and registering the first and the second image data, a boundary connecting sector is determined connecting adjacent boundaries of the first image 412, the second image 414. According to the example shown, the boundary connecting sector is a straight line, also referred to as a straight interface 416. Then, a separator 418 is generated on behalf of the image data of the boundary connecting sector, i.e. on behalf of the image data of the straight interface 416. Further, the image data of the first image 412 and the second image 414 is combined with image data of the separator 418 to a combined image data shown as a combined image 420 in FIG. 10 comprising the separator 418. For example, the separator 418 in FIG. 10 is shown as a striped line. The striped line provides the effect that a good sense of observing an uninterrupted volume is given, while still hiding discontinuities.

For an even better understanding, FIGS. 11 to 16 show photographic images of FIGS. 5 to 10 showing X-ray images arranged adjacent to each other in relation to a combined image comprising a separator, wherein the combined image is shown underneath the adjacently arranged images.

Figure 17:
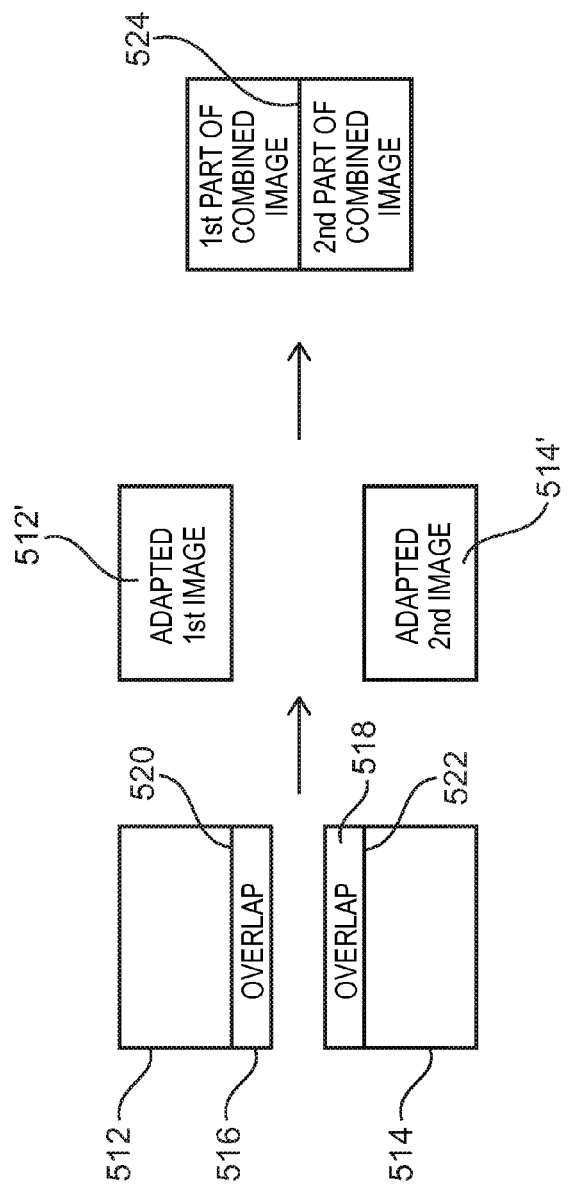
FIG. 17 schematically shows sub steps of an embodiment of the method, shown in FIGS. 2 to 4.

According to a further exemplary embodiment, the step of determining the boundary connecting sector of a first image 512 and a second image 614 comprises the following sub steps. As can be seen in FIG. 17, a common image region 516 of the first image data 512 overlapping with the second image data 514 is determined. Further, a common image region 518 of the second image data 514 overlapping with the first image data 512 is determined. Next, cutting data is determined in the common image region. In the example shown, the cutting data is a cutting line 520 in the first image 512 and a cutting line 522 in the second image 514. Next, a first image data 512 is adapted by cutting the first image data according to the cutting data that is according to the cutting line 520 removing the overlapping region 516 of the first image 512. The second image 514 is adapted by cutting the second image data 514 according to the cutting line 522 removing the overlapping region 518 of the second image 514. Thus, an adapted first image 512' and an adapted second image 514' are provided. Further, the cutting data is determined as boundary connecting sector and the separator is generated adapted to the cutting data. Still further, the image data of the first adapted image 512' is combined with the image data of the adapted image 514' together with a separator 524 and the combined image is displayed on the display.

According to another exemplary embodiment of the invention, the separator can be shown not only as a thin line, but also in other geometric forms, in case the image data is a two-dimensional image.

Figure 18:
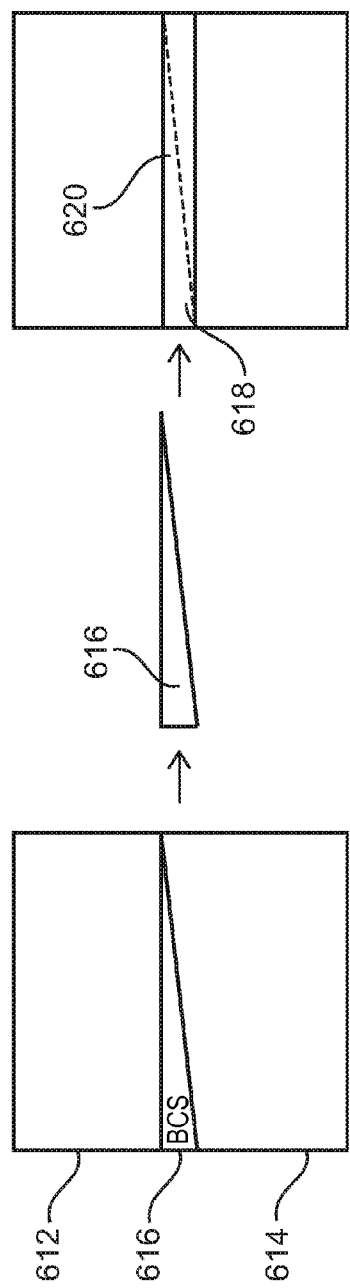
FIG. 18 schematically shows a boundary connecting sector of two adjacent images and the separator generated on behalf of the boundary connecting sector.

As a further example, FIG. 18 shows a first image 612 and a second image 614. The two images 612, 614 are already registered in FIG. 18. Nevertheless, a boundary connecting sector 616 has been determined connecting the adjacent boundaries of the first image 612 and the second image 614. As can be seen, the boundary connecting sector 616 has a form of a wedge which might be due, for example, to misalignment during the image acquisition procedure. However, in order to present an easily understandable image without disturbing graphical elements, such as discontinuities in the intensity for example, a separator 618 is generated on behalf of the image data of the boundary connecting sector 616. The separator 618 is adapted to both the boundary connecting sector 616 and to aspects relating to visible conceptance of image contents. The separator 618 is a thicker horizontal line separating the first image 612 and the second image 614. Due to the separator 618, differences in the intensity, for example, are not visible any more to the user. Further, since the separator is covering the wedge-like boundary connecting sector 616, indicated by a dotted line 620, no disturbing lines, such as small deviations in the angle or horizontal plane are shown. Thus, an image is provided covering a larger image area than just showing one image, wherein the discontinuities are removed with respect to the sense of observing an uninterrupted volume.

According to a further exemplary embodiment, not shown in the figures, the image data is three-dimensional image data and a separator is a volume that is a boundary volume connecting the adjacent volumes of the first image data and the second image data. Accordingly, the separator is, for example, a layer or plane in space that can be displayed according to the type of graphical display chosen for the three-dimensional representation on a two-dimensional stream.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

Any reference signs in the claims should not be construed as limiting the scope.

The invention claimed is:

1. A medical imaging system for generating a composite medical view combining at least first and second image data, comprising:
   an image acquisition device;
   a medical image compositing unit; and
   a display device;
   wherein the image acquisition device is configured for acquiring a first and a second image;
   wherein the medical image compositing unit is configured for:
      receiving, from the image acquisition device, first image data of said first image and second image data of said second image;
      registering the first and the second image data;
      determining a boundary connecting sector connecting adjacent boundaries of the first image and the second image;
      generating a separator on behalf of the image data of the boundary connecting sector; and
      combining image data of the first image and the second image with image data of the separator to thereby form a combined image that comprises the separator; and
   said system being configured for, via the display device, displaying the combined image, said separator, in said combined image:
   a) comprising a graphic symbol; and
   b) being colored so as to distinguish itself from its immediate background; or c) both comprising a graphic symbol and being colored so as to distinguish itself from its immediate background.

2. Medical imaging system according to claim 1, wherein an interface unit is provided; which interface unit is configured for the selection of the first image and the second image by the user.

3. Medical imaging system according to claim 1, wherein the medical image compositing unit is configured for:
   determining a common image region of the first image data overlapping with the second image data, and a common image region of the second image data overlapping with the first image data;
   determining cutting data in the common image region;
   adapting the first image data by cutting the first image data according to the cutting data;
   removing the overlapping region of the first image data;
   adapting the second image data by cutting the second image data according to the cutting data;
   removing the overlapping region of the second image data;
   determining the cutting data as said boundary connecting sector; and
   generating the separator adapted to the cutting data.

4. A medical imaging system according to claim 1, wherein the image acquisition device is an X-ray acquisition device.

5. The system of claim 4, in case said combined image has a dark background showing image information in bright colors, said displaying of said separator is in a bright color and, in case said combined image is a grey scale image, said displaying of said separator is in a bright grey scale value.

6. The system of claim 1, said separator comprising a graphic symbol.

7. The system of claim 6, said separator comprising a dotted line.

8. The system of claim 1, said separator being colored so as to distinguish itself from its immediate background.

9. The system of claim 1, in case said combined image has a dark background showing image information in bright colors, said displaying of said separator is in a bright color and, in case said combined image is a grey scale image, said displaying of said separator is in a bright grey scale value.

10. The system of claim 1, configured for creating said combined image without need for blending images together in an overlap region of said first and second images.

11. A non-transitory computer readable medium embodying a program for generating a composite medical view, said program having instructions executable by a processor for performing a plurality of acts, among said plurality there being the acts of:
- a) selecting first image data of a first image and second image data of a second image; b) registering the first and the second image data; c) determining a boundary connecting sector connecting adjacent boundaries of the first image and the second image; d) generating a separator on behalf of the image data of the boundary connecting sector; e) combining image data of the first image and the second image with image data of the separator to thereby form a combined image that comprises the separator; and f) displaying the combined image, said separator at least one of:
- a) comprising a graphic symbol; and
- b) being colored so as to distinguish itself from its immediate background.

12. A computer readable medium according to claim 11, said determining comprising:
- determining a common image region of the first image data overlapping with the second image data and determining a common image region of the second image data overlapping with the first image data;
- determining cutting data in the common image region;
- adapting the first image data by cutting the first image data according to the cutting data;
- removing the overlapping region of the first image data;
- adapting the second image data by cutting the second image data according to the cutting data;
- removing the overlapping region of the second image data;
- determining the cutting data as said boundary connecting sector; and
- said generating comprises generating the separator adapted to the cutting data.

13. A computer readable medium according to claim 11, said combining comprising displacing, in relation to each other, the first image data and the second image data, both cut according to cutting data, and locating the separator such that the separator is located at least outside the adapted first image.

14. A computer readable medium according to claim 11, wherein the image data is two-dimensional image data.

15. A computer readable medium according to claim 14, wherein the separator is a line.

16. The computer readable medium of claim 11, said separator comprising a graphic symbol.

17. The computer readable medium of claim 11, said separator being colored so as to distinguish itself from its immediate background.

18. The computer readable medium of claim 11, said combining being performed without need for blending images together in an overlap region of said first and second images.

19. Method for generating a composite medical view combining at least first and second image data with the following steps: a) selecting first image data of a first image and second image data of a second image; b) registering the first and the second image data; c) determining a boundary connecting sector connecting adjacent boundaries of the first image and the second image; d) generating a separator on behalf of the image data of the boundary connecting sector; e) combining image data of the first image and the second image with image data of the separator to a combined image data; and f) displaying the combined image comprising the separator, wherein the image data is two-dimensional image data, wherein the separator is a striped line.

20. The method of claim 19, said separator being colored so as to distinguish itself from its immediate background.

21. A medical imaging system for generating a composite medical view combining at least first and second image data, comprising:
- an image acquisition device;
- a medical image stitching unit; and
- a display device;
- wherein the image acquisition device acquires a first and a second image;
- wherein the medical image stitching unit receives, from the image acquisition device, first image data of said first image and second image data of said second image; registers the first and the second image data; determines a boundary connecting sector connecting adjacent boundaries of the first image and the second image; generates a separator on behalf of the image data of the boundary connecting sector; and combines image data of the first image and the second image with image data of the separator to thereby form a combined image that comprises the separator; and
- said system displays, via the display device, the combined image,
- said separator, in said combined image: a) comprising a graphic symbol; b) being colored so as to distinguish itself from its immediate background; or c) both comprising a graphic symbol and being colored so as to distinguish itself from its immediate background.

* * * * *